(12) United States Patent
Conti et al.

(10) Patent No.: US 9,453,788 B2
(45) Date of Patent: Sep. 27, 2016

(54) ACUTE MEDICAL PARTICULATE TESTING DEVICE

(71) Applicant: Dynatek Labs, Inc., Galena, MO (US)

(72) Inventors: James C. Conti, Galena, MO (US); Elaine R. Strope, Galena, MO (US)

(73) Assignee: DYNATEK LABS, INC., Galena, MO (US)

( * ) Notice: Subject to any disclaimer, the term of this patent is extended or adjusted under 35 U.S.C. 154(b) by 320 days.

(21) Appl. No.: 14/174,565

(22) Filed: Feb. 6, 2014

(65) Prior Publication Data

US 2014/0216181 A1 Aug. 7, 2014

Related U.S. Application Data

(60) Provisional application No. 61/762,026, filed on Feb. 7, 2013.

(51) Int. Cl.
| | |
|---|---|
| *G01N 15/02* | (2006.01) |
| *G01N 15/10* | (2006.01) |
| *G01N 15/00* | (2006.01) |
| *G01N 3/56* | (2006.01) |

(52) U.S. Cl.
CPC ............. *G01N 15/02* (2013.01); *G01N 3/567* (2013.01); *G01N 2015/0053* (2013.01); *G01N 2015/1068* (2013.01)

(58) Field of Classification Search
CPC ....................... G01N 15/02; G01N 2015/1068
See application file for complete search history.

(56) References Cited

U.S. PATENT DOCUMENTS

| | | | |
|---|---|---|---|
| 5,670,708 A | 9/1997 | Vilendrer | |
| 5,899,937 A | 5/1999 | Goldstein et al. | |
| 6,062,866 A * | 5/2000 | Prom | G09B 23/28 434/262 |
| 6,881,224 B2 | 4/2005 | Kruse et al. | |
| 7,066,038 B2 | 6/2006 | Moir et al. | |
| 7,254,988 B2 | 8/2007 | Keeble | |
| 7,313,976 B2 | 1/2008 | Swain et al. | |
| 7,581,457 B2 | 9/2009 | Bussu | |
| 7,621,192 B2 * | 11/2009 | Conti | G01N 3/56 623/912 |
| 7,886,623 B2 | 2/2011 | Yang et al. | |
| 2010/0313683 A1 * | 12/2010 | Nickel | G01N 3/12 73/863 |

* cited by examiner

*Primary Examiner* — Paul West
(74) *Attorney, Agent, or Firm* — Lathrop & Gage LLP

(57) ABSTRACT

An acute medical particulate testing device for determining particle shed from a medical device during implantation. The device includes a closed loop system through which a solution is forcibly passed. An inlet port allows a catheter-mounted medical device to be incorporated into the flow loop. At least one tortuous passage is provided to replicate the vascular pathway and tortuosity which simulates the turns and bends and rubbing that affect particulate release from an implantable medical device as it is passed through the vasculature. A debubbler is provided to remove air bubbles from the solution before it is passed into a particle counting device that counts particle shed from the medical device during the simulated implantation. A filter having desired porosity removes particles from the solution. A final filter system removes all particles and air bubbles from the solution before it is re-circulated through the loop.

13 Claims, 8 Drawing Sheets

ACUTE MEDICAL PARTICULATE TESTING DEVICE

RELATED APPLICATION

This application claims the benefit of U.S. Patent Application Ser. No. 61/762,026 filed Feb. 7, 2013, the disclosure of which is incorporated herein by reference.

BACKGROUND OF THE INVENTION

This disclosure relates to a testing device for analyzing the amount of particles shed from medical devices during implantation into or manipulation through the bodily tissues of a human being. The Food and Drug Administration has long required that device manufacturers characterize the amount of particle shedding from implantable medical devices during the lifetime of the implanted device. A number of inventions have been developed to rapidly accelerate testing conditions to artificially simulate implant conditions over a long period of time. It is known, for example, that implantable medical devices such as stents, heart valves, and in vivo blood filters tend to shed particles from material coatings or from the device material itself over long periods of time. A heart stent, for example, will experience several million heartbeat cycles throughout its implant lifetime. Several inventions allow rapid acceleration of the testing of such devices in the implanted condition. For example, a medical device durability tester will condense a lifetime of heartbeat cycles into a few years by accelerating the replicated heart cycles at a pace much faster than encountered in the normal human condition. Thus, a lifetime of heartbeats can be condensed into a much shorter period of time. Some durability testing devices incorporate particle shed counters while others rely on particulate filters to capture shed particles for microscopic counting.

While several medical device durability test units are commercially available, until now there has not been a device specifically configured to ascertain particle shed that may occur as an implant or other medical device is maneuvered into position within the human body. Medical implants delivered by catheter, such as stents, blood filters, and catheter-delivered heart valves are usually implanted through human vasculature. For example, a heart stent may be implanted through a femoral artery in a patient's inner thigh. Other devices may be manipulated through human tissues that resist movement or require tortuous manipulation of the device. Thus, the implant or other device travels a relatively long and tortuous pathway through the human vasculature or other body tissue to the implant or usage location. There is concern that the process of implanting such devices through the vasculature or other body tissue may result in particle shedding from the device due to rubbing and vasculature pressure. Further, for devices deployed via catheter, it is necessary to determine counts of particles shed from the catheter. It is important to analyze the count of particles shed during implantation as part of a medical protocol in anticipation of FDA review and approval of such devices.

Accordingly, applicant's invention substantially replicates the conditions experienced during medical device implantation through human vasculature or manipulation through body tissues. Conditions such as vasculature pressure, temperature, pH, length of implant travel, and the travel pathway must be substantially replicated for accurate testing with this invention.

BRIEF SUMMARY OF THE INVENTION

This disclosure advances the art and achieves goals outlined above by providing a testing device for medical devices, both implantable and non-implantable, to ascertain particle shed during the implant or usage procedure. The testing device accurately determines particle shed from an medical device as it is manipulated through a test apparatus that substantially replicates the environment of the human body for purposes of determine the number of particles shed from the medical device.

The testing device substantially replicates the environment of the human body by utilizing a preferred test solution and a test pathway that replicates the human vasculature or other pathway through which the medical device is to be passed during a medical procedure. Accordingly, a test pathway is provided that can be manufactured from substantially rigid tubing, glass or other suitable inert material through which a test solution can be passed. A substantially closed-loop system is presented such that the test solution can be circulated to replicate blood flow. A buffered saline, water or other suitable test solution may be utilized; however, such solution must be relatively clear for accurate particle shed counting. The test solution is maintained at a pH, temperature, and consistency similar to that of human blood. The test solution is passed through the test pathway that should ideally replicate the length of the human vasculature or other tissue through which the device will be passed during the procedure.

At least one tortuous passage is included in the test pathway. The tortuous passage simulates the turns, bends, and the rubbing effect that may contribute to shedding of particles from the medical device. The tortuous passage dimensions may be changed to more closely replicate the specific vasculature or tissue through which the device will be passed. A primary flow line is provided to supply test solution to the test pathway. The primary flow line is in fluidic communication with the test pathway so that the test solution is also provided in the test pathway. The test pathway includes a port through which the test device is deployed into the test pathway. In use, a catheter-mounted medical device is passed through the port into the test pathway. The device is passed through the tortuous passage section of the test pathway such that the effort substantially replicates actual implantation of the medical device in a human body.

The test solution circulates through the test pathway and transports any particles shed from the medical device into the primary flow line. A particle counting mechanism is positioned downstream from the test pathway and the tortuous passage. Various particle counters, such as laser particle counters, are known and one such particle counter or multiple particle counters may be used to achieve accurate particle counts dependent on the experimental flow rate of the test solution. For example, many laser particle counters can only process a flow rate of 100 mL/min for accurate particle counting. The use of five separate laser particle counters allows up to 500 mL/min flow rate with accurate counting. Actual flow rate for the test device is controlled by flow meters so that realistic flow rate can be achieved while still operating within the available parameters of the particle counters.

It is also preferred to remove as many bubbles as possible from the test solution prior to passing the solution through the particle counters. The preferred test device includes a custom debubbler that substantially removes all air bubbles from the test solution before the test solution passes to the particle counters. The debubbler includes a series of extremely fine mesh stainless steel filters, spaced apart within a column through which the test solution is forced. In one embodiment, each stainless steel mesh filter preferably has openings of approximately 0.030×0.013 inches to control filtration capability. This porosity does not impede flow of the test solution while removing the vast majority of bubbles.

The device many also incorporate a particle collection filter system. Solution flow from the particle counters will be collected together and delivered into a particle collection filter system. The filter can accept any number of different filters with selected porosity depending on the size requirements of the test being conducted. Filters are positioned downstream from the particle counters to substantially remove any particles from the solution flow so that they are not recirculated back through the primary line to the particle counters. The filters may be collected at the end of the experiment and reviewed with scanning electron microscopy or other similar means to further evaluate particle shed rates, count and size, along with elemental analysis of the shed particles to determine particle origination.

The preferred condition of the solution for testing is generally maintained by computer control. A temperature sensor is deployed into the device at a preferred location, such as at the debubbler, and communicates with the computer for the maintenance of a desired temperature in the test solution using a heater provided on the capacitance tank for the system. A computer-regulated fluid pump maintains sufficient solution pressure to operate the system. The fluid pump may operate in a pulsatile manner to replicate the operation of the human heart. An air pump may be used to maintain systemic pressures that might be necessary during the experiment. The computer control system controls and monitors all experimental parameters and records and stores all data including particulate data from the particle counters. Particulate data is counted and sorted by count and size and is stored in a desired electronic fashion. The frequency of data acquisition is variable and can be chosen by the user.

In some embodiments, a filter system is positioned immediately upstream from the fluid pump for cleaning of the test solution before recirculation through the test pathway. In some embodiments, the filter has a 0.2 micron filter that ensures no particulates and no air bubbles larger than 0.2 microns are delivered back to the test pathway.

It is also possible to vary flow rate to the particle counter system without increasing flow pressure through the primary flow line or test pathway. This is achieved by having a series of small inter-connected tubes that can be brought into line with the closed loop to increase flow rate. By increasing the flow rate, there is a reduction in the total time it takes to complete the particle experiment. However, this often increases the chances of delivering air bubbles into the particle counter.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings.

DETAILED DESCRIPTION

The present disclosure may be understood by reference to the following detailed description taken in conjunction with the figures as briefly described herein.

Figure 1:
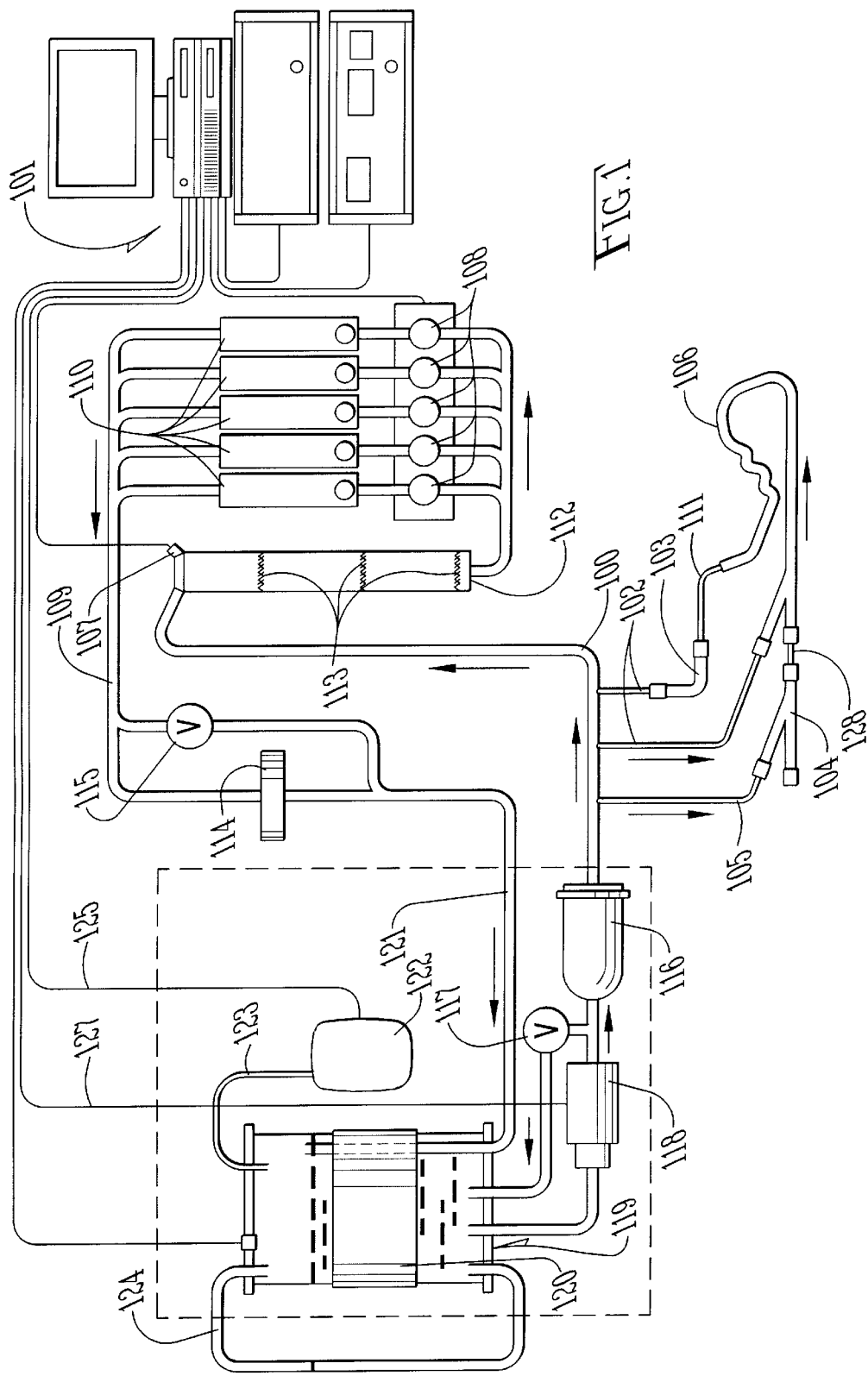
FIG. 1 is a schematic view of an embodiment of the testing device.

The disclosure provides a testing device for medical devices that comprises various interconnected systems, namely a computer control system, a substantially closed loop fluid pathway, and a human tissue simulation assembly as shown schematically in FIG. 1. The inventive device is intended to replicate the conditions of human vasculature or other tissue into which a medical device may be deployed, positioned, and implanted for health care benefits. Such devices are well-known and include a variety of stents, artificial heart valves, and blood filter systems. The devices are generally catheter-delivered through a patient's artery or vein. In other embodiments the devices to be tested may include devices not intended for use in human vasculature, such as hip implants, artificial joints, devices for use in the airways, bile ducts or urinary tracts and other similar devices.

Referring now specifically to FIG. 1, a schematic view of the testing system is depicted. The flow of test solution through the system is generally depicted by arrows adjacent to the various fluid lines comprising the testing system. The system comprises a substantially closed loop system whereby test solution is pumped through the system and then recirculated. The test solution is intended to simulate certain characteristics of blood and is maintained at a preferred temperature, pH, viscosity, and flow rate. Flow may be pulsatile to simulate arterial blood flow.

The closed loop fluid pathway includes a primary flow line 100 to deliver a fluid or solution to a test pathway 102. The test pathway 102 comprises a hollow tube that can be plastic, glass, or other suitable inert material, or combinations of the foregoing, that substantially mimic the size and overall geometry of a human artery, vein or other structure or pathway through human tissue. The primary flow line 100 and the test pathway 102 comprise a substantially closed pathway for the test solution. A portion of the test solution flowing through primary line 100 will flow into the upstream end of test pathway 102 and back into primary line 100 at the downstream end of test pathway 102.

A port 104 is provided into which the medical device to be tested is deployed. For example, a catheter-delivered stent would be inserted into an introducer port 104 to simulate the passage of the medical device into the human vasculature for implantation. The introducer port 104 substantially replicates the port assembly as utilized by physicians to initially insert catheter-delivered medical devices into the vasculature. In one embodiment, the introducer port is a Tuohy-Borst sidearm introducer port. The introducer port 104 is in fluidic communication with the test pathway 102. The introducer port 104 may be provided with a sidearm port connected to the primary flow line via tubing 105 to allow test solution to flow from the primary line 100 into introducer port 104. When testing other devices, a different port 104 may be utilized as necessary to insert the medical device into the test pathway 102. Additional tubing typically connects the output of the port 104 to tortuous pathway 106.

Figure 2:
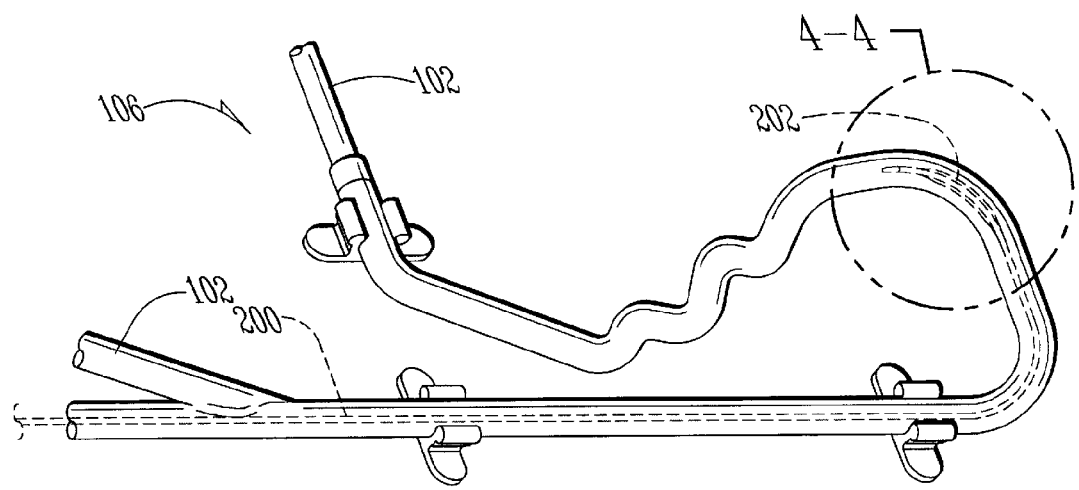
FIG. 2 is a perspective view of an embodiment of the tortuous passage portion of the test pathway.

As shown in FIG. 1 and in detail in FIG. 2, at least one tortuous pathway 106 is incorporated into the test pathway 102. The tortuous pathway 106 substantially replicates the pathway and tortuosity which simulates the turns and bends and rubbing that may affect particulate release from a device or delivery system targeting a specific area of the human vasculature or other location within the body. The depicted tortuous pathway 106 substantially simulates the arteries leading to the left anterior descending artery of the heart, a common placement target for stents. Other geometries of the passage 106 may be used to simulate other portions of the human body.

Figure 3:
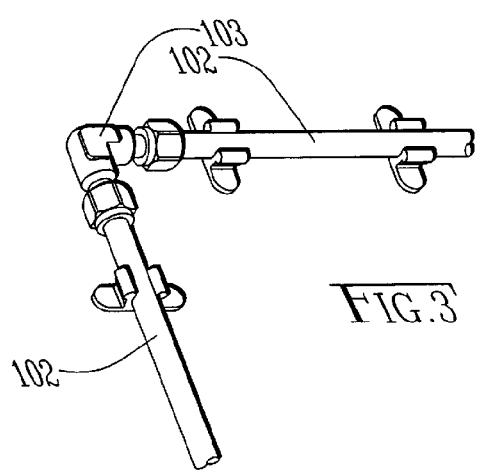
FIG. 3 is a perspective view of an embodiment of a portion of the test pathway.

Because the vascular distance for medical device deployment varies among patients and varies as to the intended implantation site of the device, it is beneficial to test the medical device through varying lengths of test pathway 102 which affects the flow rate of the test solution. The interconnected tube assembly is best shown at FIGS. 1 and 3. Test pathway 102 may be provided with joints 103 to allow the length of test pathway 102 to be modified by the addition of additional lengths of tubing, or tubing of different sizes, shapes or configurations.

In some embodiments, an area 111 between tortuous passage 106 and fitting 103 may be provided for deployment or operation of the medical device. For example, a simulated artery may be connected in area 111 to allow a stent to be placed in the mock artery after being inserted through tortuous passage 106. This allows the system to test shed rates during insertion and also operation of the medical device.

In some embodiments, the length of the test pathway 102 may also be changed by using interconnected tubing that can be selectively brought into the test pathway 102 between introducer port 104 and tortuous passage 106. In some embodiments, tube 128 may be varied in length to simulate an appropriate insertion distance for the medical device before the tortuous passage 106.

Figure 4:
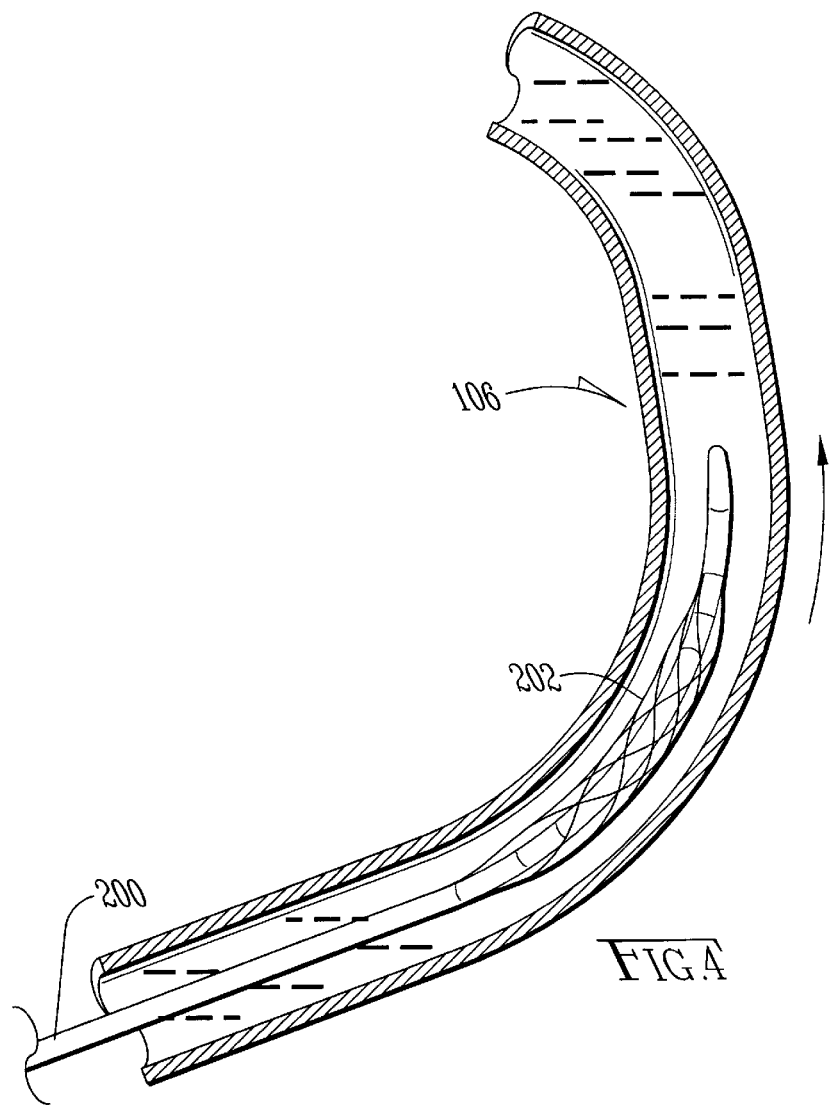
FIG. 4 is a cross-sectional view of an embodiment of a portion of the tortuous pathway.

As depicted in FIG. 2 and in detail in FIG. 4, a catheter 200 has been inserted through port 104 into test pathway 102. The distal end of catheter 102 comprises stent 202 for implantation beyond tortuous pathway 106. As the catheter 200 and stent 202 are maneuvered through the tortuous pathway 106, the bending, flexing and rubbing of the device may cause particles to shed from the device and be carried away by the test solution in the test pathway 102. It is understood that the configuration of the tortuous pathway 106 will be modified to simulate the vasculature or other body tissue through which the medical device being tested would commonly traverse during implantation or usage.

The medical device is forced through the tortuous pathway 106 and through the test pathway 102 for a distance commensurate with the length of the vasculature or other tissue through which the medical device is anticipated to pass for implant or usage. In the depicted example, a catheter mounted stent is inserted through the introducer port 104 and into test pathway 102. The stent is then inserted through the test pathway 102 and through tortuous pathway 106 to simulate the insertion and positioning of the device during actual usage on a patient. The medical device may be inflated, operated or otherwise activated to test the use and deployment of the device after insertion in mock artery 111.

Figure 5:
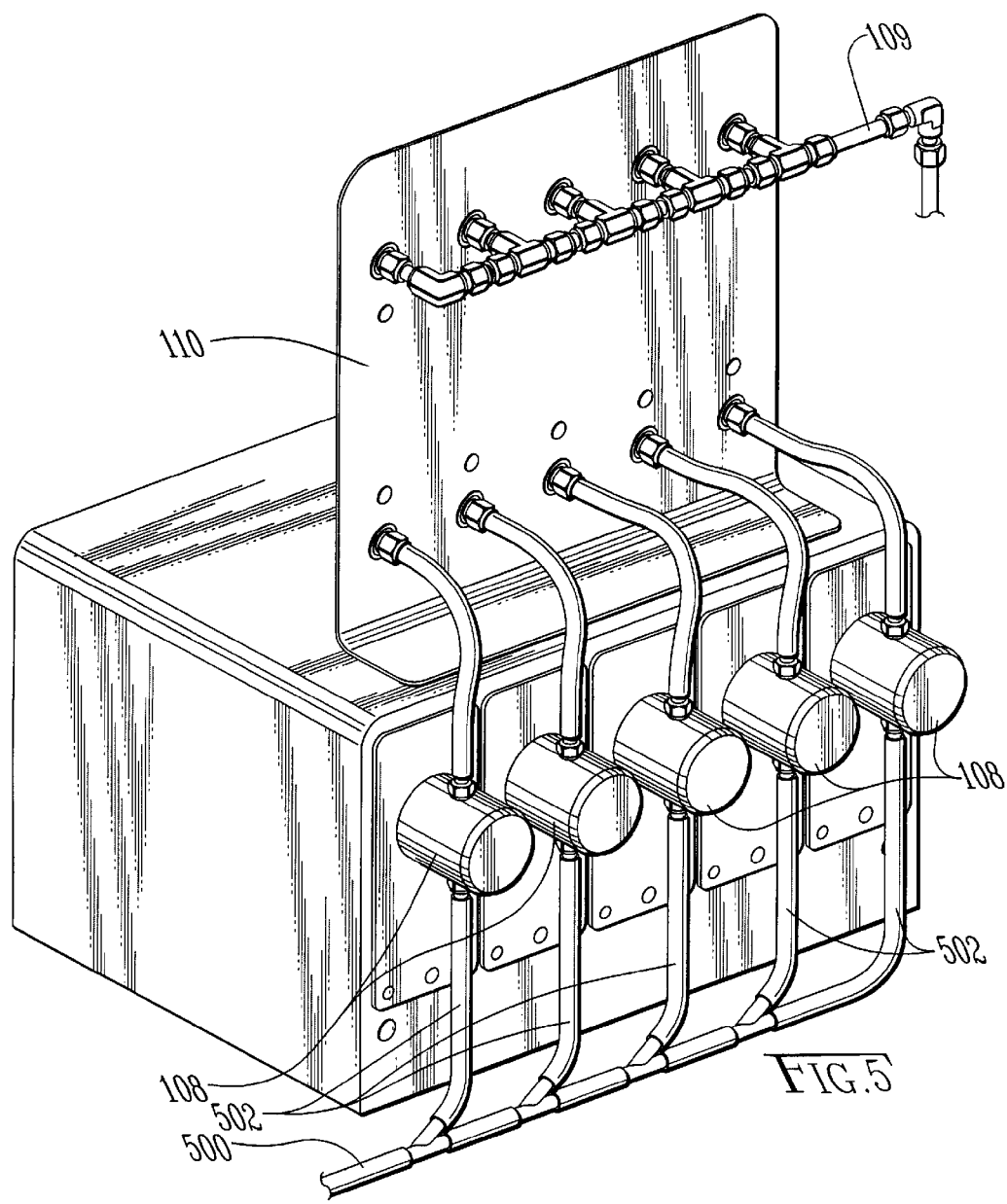
FIG. 5 is a perspective view of a portion of an embodiment of the testing device, namely the particle counters.

It is the number and size of particles shed during the passage of the medical device through the port 104 into the test pathway 102 and through the tortuous pathway 106 that is of interest. Accordingly, the test data sought is the number and size of particles shed from the medical device during this portion of the procedure. The test solution carries any particulates shed during the procedure through the test pathway 102 to primary flow line 100 which is connected to particle counters 108. Particle counters 108 may be any technology suitable for counting and sizing, or measuring the size of, particles suspended in the test solution, such as laser particle counters that are available on the market. Referring now to FIG. 5, a cabinet containing five laser particle counters 108 is depicted, connected in parallel to the output 500 of primary flow line 100 (after passing through the debubbler as described in relation to a later figure). The fluidic output of each particle counter 108 is connected to a flow meter 110 described in relation to a later figure.

Figure 6:
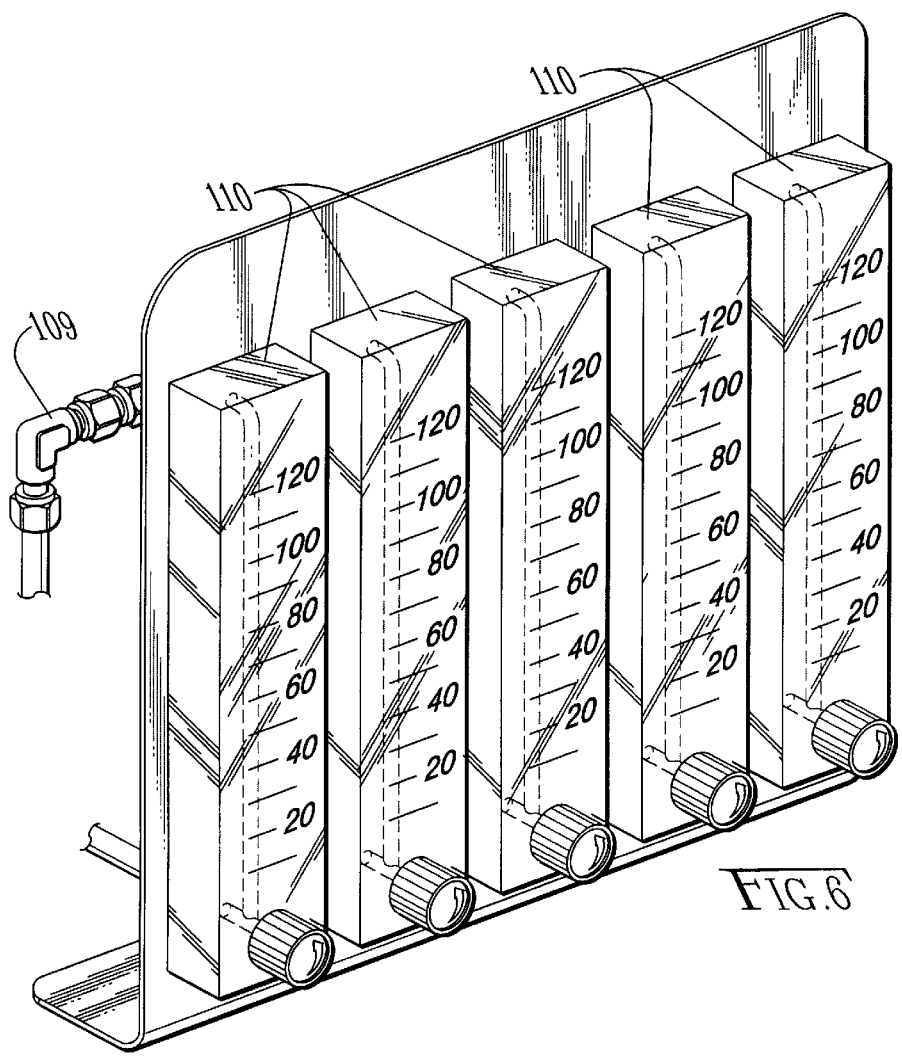
FIG. 6 is a perspective view of a portion of an embodiment of the testing device, namely a flow meter component.

In some embodiments of the system, accurate particle counting and sizing is best achieved at a flow rate of 100 mL of test solution or less per minute through each particle counter. Multiple particle counters can be provided in parallel to increase the flow rate that may be tested through the system. As shown, five particle counters 108 are provided in parallel to increase the test flow rate to 500 mL/min, achieved at a 100 mL/min rate per counter 108. In some embodiments of the testing system, flow meters 110 may be provided to measure and control the flow through each particle counter to prevent miscounting of particles due to excessively high flow rates. Referring to FIGS. 5 and 6 an array of flow meters 110 is provided to independently measure and control the flow rate through each particle counter 108. Each flow meter 110, though an adjustable valve or similar mechanism, may allow the manual adjustment of individual flow rates through a particular particle counter. The output of all flow meters 110 are combined into a single output line 109 which carries the flow of test solution to the remainder of the testing system.

Figure 7:
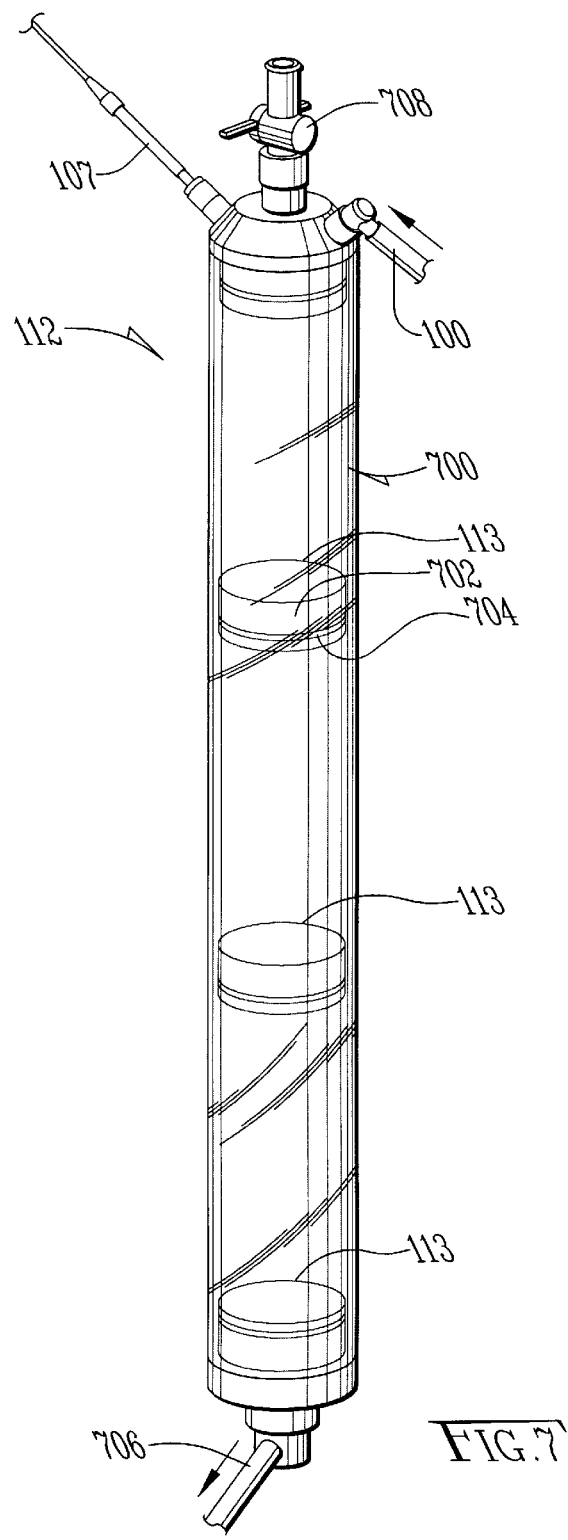
FIG. 7 is a perspective view of a portion of an embodiment of testing device, namely a debubbler component.

Particle counting and sizing accuracy can be adversely affected by air bubbles in the test solution. To minimize air bubbles in the solution before counting, a debubbler 112 may be installed as shown in FIG. 1 and in detail in FIG. 7. The debubbler 112 comprises a column 700, in some embodiments a transparent plastic or glass having a cylindrical cross-section, having at least one fine mesh stainless steel filters 113 spaced apart along the length of the column 700. In some embodiments, the filters 113 are evenly spaced along the column 700, though it other embodiments they may be unevenly spaced.

In some embodiments, the fine mesh stainless steel filters 113 provide filtration via a 0.030×0.013 inches mesh. The filters 113 substantially capture the bubbles present in the test solution to maximize the effective particle counting capabilities of the downstream particle counters 108 without impeding flow rate through the primary flow line 100 or the test pathway 102. In some embodiments the filters 113 are secured in collars 702 and sealed to column 700 via o-rings 704. The test solution flows into debubbler 112 from primary flow line 100 and exits from the output flow line 706 disposed near the bottom of the column 700. A valve 708 may be provided at the top of the column 700 to allow collected bubbles to be released from the testing system. In some embodiments, a temperature sensor 107 is incorporated into the debubbler 112 to measure the temperature of the test solution, though the temperature sensor may be separately provided apart from the debubbler 112 in some embodiments.

Figure 8:
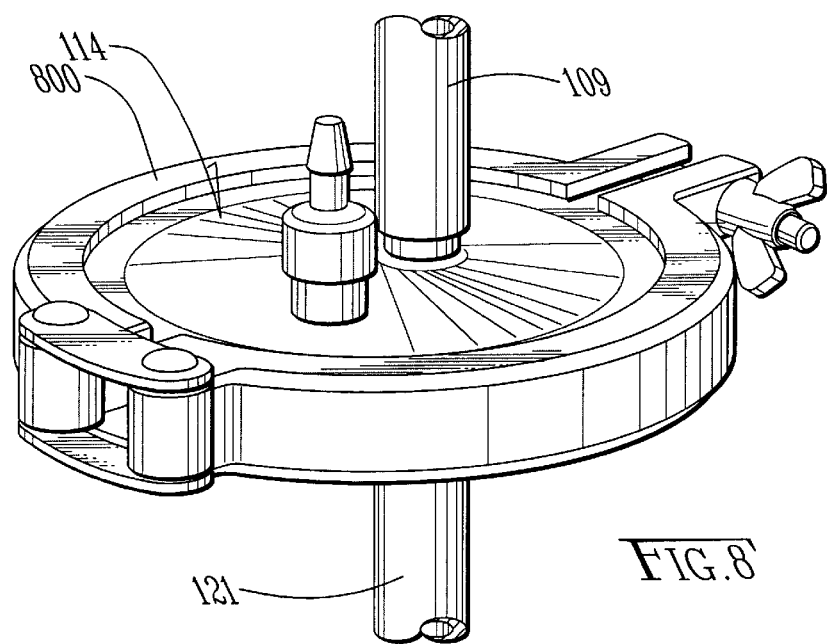
FIG. 8 is a perspective view of a portion of an embodiment of the testing device, namely a filter component.

After the test solution has passed through the particle counters 108, it is necessary to collect any particles from the test solution to prevent them from flowing back through the test pathway 102. As shown in FIG. 1 and FIG. 8, a particle collection filter 114 may be provided to collect the particles from the test solution. The test solution flows through line 109 into filter 114 and out through line 121. The particles collected by filter 114 may also be counted via a microscope as an additional testing method. The filter configuration may change depending upon the parameters of the test data desired by the user. Filters having different pore size collect only those shed particles of interest for the test. In some embodiments a filter 114 is used with a removable collar 800 to allow the filter media to be removed for replacement or analysis of particle count.

The filter 114 may also be bypassed by bypass valve 115 if no collection of particles is desired. Smaller particles that pass through the particle collection filter unit 114 are ultimately captured by the filtration system 116 described in relation to a later figure.

Figure 9:
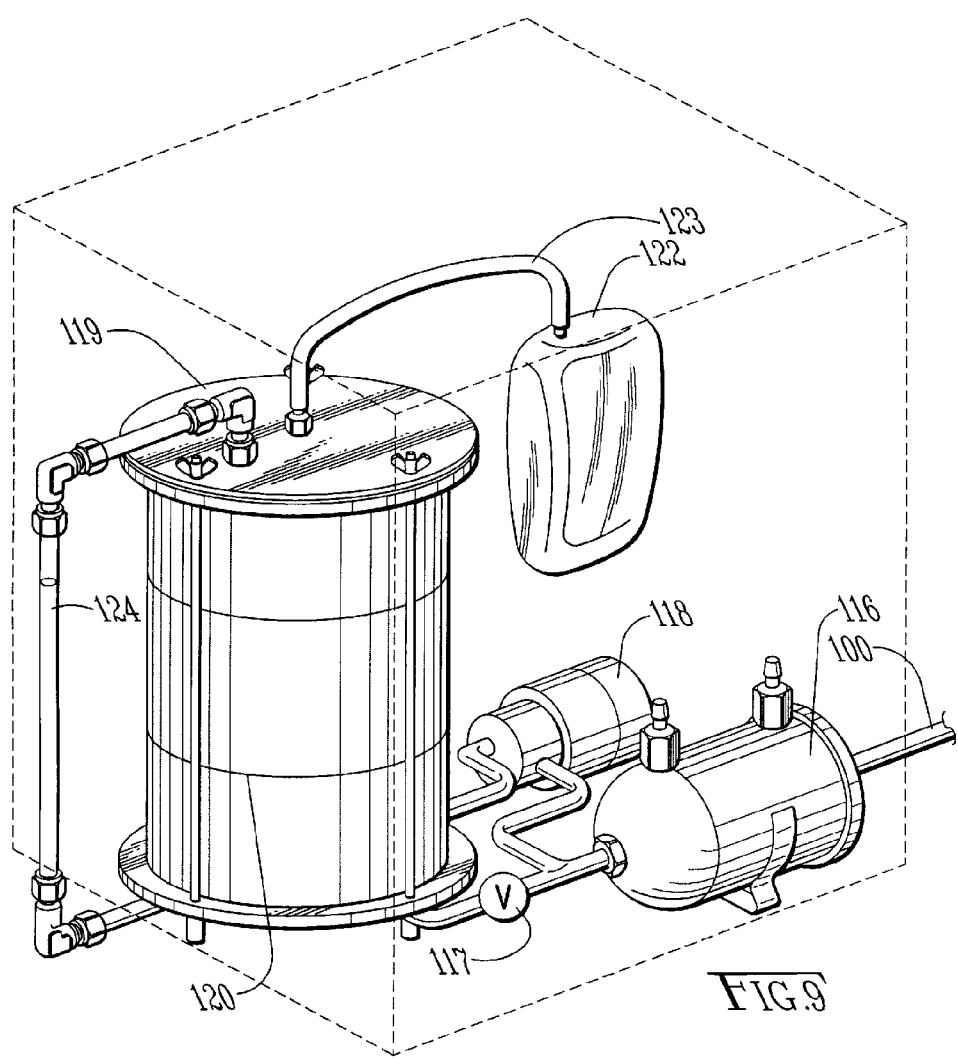
FIG. 9 is a perspective view of a portion of an embodiment of the testing device, namely the capacitance tank and pump assembly.

Referring now to FIGS. 1 and 9, after passing through filter 114 or bypass valve 115, the test solution flows through line 121 into capacitance tank 119. Capacitance tank 119 provides a reservoir of test solution that may be pumped through the primary flow line 100. The capacitance tank 119 may be provided with tube 124 to allow external checking of the level of test solution in the tank 119. Tube 124 may be transparent or may be provided with transparent portions to allow the viewing of the test solution level.

Capacitance tank 119 may be provided with a heater element 120 that may be internally or externally attached to the tank 119. The heater 120 is controlled by computer control system 101 via a control line to heat the test solution as necessary to maintain a desired temperature as may be measured by temperature sensor 107.

The capacitance tank 119 also contains some amount of air or other inert gas. The gas within the tank 119 is pressurized by air pump 122 through air line 123. This pressure on the fluid in tank 119 provides a desired systemic pressure throughout the fluid in the testing system. The air pump 122 is controlled by computer control system 101 via connection 125 based on readings from pressure sensors provided at one or more desired positions within the testing system. Other elements of the system such as flow meters 110 could be monitored and controlled by the computer system 101 in other embodiments of the system.

Fluid pressure for the system is achieved by a fluid pump 118, which is electronically connected to the computer control system 101 via connection 127. Pump 118 accepts test solution held in capacitance tank 119 and pumps it toward filter 116. In one embodiment, the filtration system 116 includes a 0.2 micron filter to insure that no particulates or air bubbles larger than 0.2 microns are delivered back to the primary flow line 100 or test pathway 102.

Some of the test solution flows through filter 116 and back into primary flow line 100 and is recirculated through the previously described testing system. Some of the test solution may be pumped back through valve 117 into capacitance tank 119. The valve 117 may be adjusted to alter the flow characteristics of the testing system.

The computer 101 controls and monitors all experimental parameters such as fluid pressure, temperature, and particle shed count. The computer control system 101 collects the data regarding particle shed count, sorts the data by particle count and particle size along with the frequency of data acquisition and all other variables set by the user.

Additional controls connected to and monitored by system 101 may, in embodiments, include a temperature sensor 107 attached to debubbler 112 or elsewhere in the testing system, air pump 122 and a solution heater 120. These devices, the temperature sensor 107 and solution heater 120 are all connected to and controlled by the computer control system 101.

While the inventive device has generally been described as for the embodiment and use with a catheter-deployed stent, it is to be understood that any medical devices can be tested for particle shed with this unit. While the unit is not configured for durability testing, the test pathway 102 can be altered in length and size to accommodate virtually any medical device. The tortuous pathway 106 can be configured to replicate the pathway for medical devices through human vasculature or other bodily tissues regardless of curvature, length, and size. Multiple tortuous pathways 106 may be combined for more accurate replication of the vasculature or other tissue through which the device is intended to be implanted or manipulated.

A method for determining particulate shed from a medical device during implantation or other manipulation in body tissue is achieved by passing the medical device to be tested through the introducer port 104 into the test pathway 102 of the device described herein. In one embodiment, a catheter-mounted device is advanced through the test pathway 102 into the at least one tortuous pathway 106 and through the pathway 102 a preferred distance. That preferred distance may replicates the vasculature distance through which the medical device would be implanted into a patient. The method further includes the step of counting shed particles with one or more particle counters 108, capturing shed particles in a filtration assembly 114 having preferred porosity to capture the size of particles of interest for the test and then cleaning the test solution with a filtration mechanism 116. Additional steps within the method include achieving a preferred systemic pressure and temperature to replicate the human condition during implant procedures.

Having described the preferred embodiment and a method for using the inventive device, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

It should thus be noted that the matter contained in the above description or shown in the accompanying drawings should be interpreted as a descriptive and not in a limiting sense. The following claims are intended to cover all generic and specific features described herein, as well as all statements of the scope of the present method and system which as a matter of language might be said to fall there between.

What is claimed is:

1. A system for testing a medical device comprising:
   a primary flow line in fluidic communication with a test pathway comprising a substantially closed pathway for a test solution;
   a port in the test pathway for inserting a medical device into the test pathway;

at least one tortuous passage within the test pathway through which a medical device may be passed;

at least one particle counter in fluidic communication with the primary flow line for counting and sizing particles in the test solution shed from a medical device passed through the at least one tortuous passage and a debubbler within the primary flow line between the test pathway and the at least one particle counter wherein the debubbler captures air bubbles in the test solution.

2. The system of claim 1 wherein the debubbler further comprises a column provided with at least one fine mesh filter disposed across the column.

3. The system of claim 2 further comprising a computer control system for receiving data from the at least one particle counter.

4. The system of claim 3 further comprising a capacitance tank comprising a container for holding test solution, a heater attached to the container for maintaining the test solution at a preferred temperature, and an air pump pneumatically connected to the container for adjusting the air pressure within the container.

5. The system of claim 4 further comprising a particle filtration system in fluidic communication with the primary flow line for capturing particles shed from a medical test device.

6. The system of claim 1 wherein each of the at least one particle counter may be selectively connected to the primary flow line to provide for a desired flow rate through the primary flow line.

7. A method for testing a medical device using the system of claim 1 comprising the steps of:
pumping the test solution through the substantially closed pathway;
inserting the medical device through the port into the test pathway;
forcing the medical device through the at least one tortuous passage; and
counting and sizing the particles shed by the medical device with the at least one particle counter.

8. The method of claim 7 wherein the test solution is pumped through the substantially closed pathway in a pulsatile manner.

9. The method of claim 8 further comprising the step of maintaining the test solution at a systemic pressure by pressurizing the air within a tank of test solution in fluidic communication with the primary flow line.

10. The method of claim 8 wherein the test solution is maintained at a temperature and pH similar to human blood.

11. The method of claim 8 wherein the size and shape of the tortuous passage simulates a portion of the vasculature or ducts in a human body.

12. The method of claim 11 further comprising the steps of filtering the test solution to capture the particles in the test solution.

13. A testing system for a medical device, comprising:
a test solution maintained at a preferred pressure and temperature;
a substantially closed pathway through which the solution is forcibly circulated;
an introducer port in fluidic communication with the closed pathway through which a medical device may be deployed into the pathway;
at least one tortuous passage within the pathway through which a medical device may be forcibly passed;
at least one particle counter in fluidic communication with the pathway to count and size any particles shed from the test device as it is passed through the tortuous passage;
a particle filter system having at least one filter with predetermined porosity for capturing particles shed from the medical device; and
a debubbler device disposed in the pathway between the tortuous pathway and the at least one particle counter to substantially remove air bubbles from the test solution, the debubbler device including at least one fine mesh filter for capturing bubbles in the solution.

* * * * *